United States Patent
Calhoun et al.

[19]

[11] Patent Number: 6,159,596
[45] Date of Patent: Dec. 12, 2000

[54] SELF MATING ADHESIVE FASTENER ELEMENT ARTICLES INCLUDING A SELF MATING ADHESIVE FASTENER ELEMENT AND METHODS FOR PRODUCING AND USING

[75] Inventors: Clyde D. Calhoun, Stillwater; Jennifer M. Aamodt, Woodbury, both of Minn.

[73] Assignee: 3M Innovative Properties Company, St. Paul, Minn.

[21] Appl. No.: 08/996,954

[22] Filed: Dec. 23, 1997

[51] Int. Cl.[7] .............................. A61F 13/16; C09U 7/02; B32B 3/06
[52] U.S. Cl. ............................. 428/343; 24/304; 24/575; 24/DIG. 11; 604/389; 604/391
[58] Field of Search ...................... 428/99, 343; 24/304, 24/575, DIG. 11; 604/389, 391

[56] References Cited

U.S. PATENT DOCUMENTS

| | | |
|---|---|---|
| 2,144,755 | 1/1939 | Freedman . |
| 2,499,898 | 3/1950 | Anderson . |
| 2,717,437 | 9/1955 | Mestral . |
| 3,009,235 | 11/1961 | Mestral . |
| 3,173,184 | 3/1965 | Ausnit . |
| 3,182,345 | 5/1965 | Smith . |
| 3,192,589 | 7/1965 | Pearson . |
| 3,266,113 | 8/1966 | Flanagan, Jr. . |
| 3,335,774 | 8/1967 | Reed . |
| 3,408,705 | 11/1968 | Kayser et al. . |
| 3,497,925 | 3/1970 | Brumlik . |
| 3,899,805 | 8/1975 | McMillan . |
| 3,943,609 | 3/1976 | Egan, Jr. ................................ 428/41.5 |
| 4,576,850 | 3/1986 | Martens . |
| 4,581,792 | 4/1986 | Spier . |
| 4,699,622 | 10/1987 | Toussant et al. . |
| 4,743,242 | 5/1988 | Grube et al. . |
| 4,817,816 | 4/1989 | Leseman et al. . |
| 4,819,309 | 4/1989 | Behymer . |
| 4,846,815 | 7/1989 | Scripps . |
| 4,861,635 | 8/1989 | Carpenter et al. . |
| 4,875,259 | 10/1989 | Appeldorn . |
| 4,959,265 | 9/1990 | Wood et al. . |
| 5,071,363 | 12/1991 | Reylek et al. . |
| 5,088,164 | 2/1992 | Wilson et al. . |
| 5,097,570 | 3/1992 | Gershenson . |
| 5,113,555 | 5/1992 | Wilson et al. . |
| 5,158,557 | 10/1992 | Noreen et al. . |
| 5,201,101 | 4/1993 | Rouser et al. . |
| 5,221,276 | 6/1993 | Battrell . |
| 5,636,414 | 6/1997 | Litchholt . |
| 5,888,335 | 3/1999 | Kobe et al. ........................ 428/343 X |

FOREIGN PATENT DOCUMENTS

| | | |
|---|---|---|
| WO 94/21742 | 9/1994 | WIPO . |
| WO 95/03723 | 2/1995 | WIPO . |
| WO 95/11945 | 5/1995 | WIPO . |

*Primary Examiner*—Daniel Zirker
*Attorney, Agent, or Firm*—Paul W. Busse; Scott A. Bardell

[57] ABSTRACT

A self mating adhesive fastener element is described. The self mating adhesive fastener element includes a plurality of posts each having a base, an extension, and a nontacky tip. The posts are arranged to provide a self mating pattern and fastener selectivity. An adhesive layer is provided having a first surface and a second surface. The first surface provides a tacky surface between the posts. The second surface provides for adhering the self mating adhesive fastener to a substrate. Additionally disclosed are articles which incorporate the self mating adhesive fastener element and methods for manufacturing and using the self mating adhesive fastener element.

20 Claims, 4 Drawing Sheets

SELF MATING ADHESIVE FASTENER ELEMENT ARTICLES INCLUDING A SELF MATING ADHESIVE FASTENER ELEMENT AND METHODS FOR PRODUCING AND USING

FIELD OF THE INVENTION

The invention relates to self mating adhesive fastener technology. More particularly, the invention relates to self mating adhesive fastener elements, articles including a self mating adhesive fastener element, methods for producing self mating adhesive fastener elements and articles, and methods of using self mating adhesive fastener elements and articles.

BACKGROUND OF THE INVENTION

Various types of fasteners for attaching articles together by adhesive and/or mechanical interaction are described in the art. Exemplary of fasteners that use adhesives as part of the active closure surface are disclosed in U.S. Pat. No. 4,699,622 to Toussant et al.; U.S. Pat. No. 4,743,242 to Grube et al.; U.S. Pat. No. 4,817,816 to Leseman et al.; U.S. Pat. No. 4,861,635 to Carpenter et al.; U.S. Pat. No. 4,959,265 to Wood et al.; U.S. Pat. No. 5,158,557 to Noreen et al.; and U.S. Pat. No. 5,221,276 to Battrell et al. Mechanical fasteners take on a variety of forms. One exemplary type includes fasteners having a single protrusion-receptor pair. This type of fastener is illustrated by the common metal snap. Examples of molded or extruded plastic fasteners which utilize protrusion-receptor pairs can be found in U.S. Pat. No. 2,144,755 to Freedman; U.S. Pat. No. 3,173,184 to Ausnit; U.S. Pat. No. 3,182,345 to Smith; U.S. Pat. No. 3,335,774 to Reed; and U.S. Pat. No. 4,819,309 to Behymer. The Behymer patent indicates that the two parts of the fastener can be identical thereby creating what is referred to herein as a self mating fastener.

Contrasted with mechanical fasteners that have ore or two engaging elements are fasteners that have a multiplicity of such elements. One grouping of such fasteners includes the hook-and-hook fastener described in U.S. Pat. No. 2,717,437 to Mestral, the hook-and-loop further described in U.S. Pat. No. 3,009,235 to Mestral, and the headed stem or mushroom-and-loop further described in U.S. Pat. No. 4,846,815 to Scripps.

Another grouping of fasteners using a multiplicity of engaging elements are those that predominantly have solid protrusions including of a stem and an expanded region or head at the stem tip. The expanded region or head can have a wide variety of shapes. Normally these fasteners are self mating wherein the head portion is larger in diameter or cross section than is the space between heads. Exemplary patents describing this type of fasteners include, for example, U.S. Pat. No. 2,499,898 to Anderson; U.S. Pat. No. 3,192,589 to Pearson; U.S. Pat. No. 3,266,113 to Flanagan, Jr.; U.S. Pat. No. 3,408,705 to Kayser et al.; and U.S. Pat. No. 5,097,570 to Gershenson.

U.S. Pat. No. 3,899,805 to McMillan teaches the use of headed hollow protrusions. This type of fastener includes an expanded region filting into a seat above which is a reduced cross section or restricted pocket and/or by flexing of the stem. Joining of this type of fastener is normally associated with a single or double snap as the fastener is seated.

Another type of fastener having a multiplicity of intermeshing solid protrusions is described by U.S. Pat. No. 4,875,259 to Appeldorn. In this type of fastener, the tips of the protrusions are not expanded or headed. The bond is created by the frictional forces generated between contacting surfaces of the intermeshing protrusions where the surfaces are optically smooth flats. Examples of fasteners in this third grouping can be found in U.S. Pat. No. 5,071,363 to Reylek et al.; U.S. Pat. No. 5,088,164 to Wilson et al.; U.S. Pat. No. 5,113,555 to Wilson et al.; and U.S. Pat. No. 5,201,101 to Rouser et al. A fastener based on projections that perforate the web and alternate in rows from one side of the web to the other is disclosed in U.S. Pat. No. 4,581,792 to Spier. This fastener functions by engaging the projections in the receptacles to form a releasable friction fit.

SUMMARY OF THE INVENTION

A self mating adhesive fastener element is provided by the present invention. The self mating adhesive fastener element includes a plurality of posts and an adhesive layer. Each post includes a base, an extension, and a tip. The posts are arranged on a first surface of the adhesive layer to provide a self mating pattern exhibiting fastener selectivity. The bases of the posts are attached to a first surface of the adhesive, and the posts tips extend away from the adhesive. The portion of the first surface of the adhesive between the posts is a tacky surface. A second surface of the adhesive layer is provided for adhering the self mating adhesive fastener element to a substrate.

The surface area of the self mating adhesive fastener element defined by the posts and the tacky surface provides a mating surface. It is this mating surface which can engage a mating surface of another self mating adhesive fastener element. Two engaged self mating adhesive fastener elements can remain attached until pulled apart and can then be reattached. In this manner, the self mating adhesive fastener element of the invention can be referred to as refastenable.

An article which incorporates the self mating adhesive fastener element of the invention is provided by the present invention. The second surface of the adhesive layer of the self mating adhesive fastener element is provided for bonding to a substrate. When it is bonded to a substrate, the entire structure can be referred to as an article. Exemplary articles include envelopes, clothing, textiles, closures, and plastic parts for automobiles.

A method for manufacturing a self mating adhesive fastener element is provided by the present invention. The method includes a step of providing a release liner including a plurality of recesses and a land area arranged to provide a self mating pattern exhibiting fastener selectivity. Another step includes filling the recesses of the release liner with a post forming composition to provide filled recesses. The post forming composition is preferably a composition which will cure to provide a nontacky surface adjacent the release liner. Another step includes providing an adhesive layer over the release liner covering the land area and filled recesses.

A method for using a self mating adhesive fastener element is provided by the present invention. The method includes a step of providing a self mating adhesive fastener element and applying the second surface of the adhesive layer to a substrate. The release liner can be peeled away to expose the mating, surface which can then engage the mating surface of an opposed self mating adhesive fastener element.

In this application:

"adhesive" refers to the adhesive composition, and may also refer to the adhesive layer;

"substrate" means the surface upon which the self mating adhesive fastener element is applied;

"tack" means instant contact adhesion between the adhesive and another surface which may be the posts of another fastener or a substrate, and the tack may be substrate specific; and "refastenable" means that the self mating adhesive fastener can provide at least about 3 cycles of engagement and disengagement in a 24 hour period without suffering more than a 20% decrease in peel strength and without showing cohesive failure in the adhesive. Cohesive failure is characterized by a breakdown or separation of the adhesive layer. In addition, the fastener can be provided so that the disengagement force increases with time to a generally maximum value.

Detailed Description

The adhesive fastener elements of the present invention are self mating. That is, they can be attached to two substrates to provide fastening between the substrates along the mating surfaces of the adhesive fastener elements. By utilizing the self mating adhesive fastener elements of the present invention, it is possible to inventory only one fastener element construction for use in attaching to substrates because the fastener element will bond to itself It is not necessary to provide two structurally different fastener elements. One or more self mating adhesive fastener elements of the present invention in combination with a substrate can interact to form "self mating adhesive fasteners", which, for the sake of simplicity, may be referred to as "fasteners."

The fasteners of the invention can provide fastener selectivity. By fastener selectivity, it is meant that the self mating adhesive fasteners can be, constructed so they attach only to surfaces having the configuration or structure which fits or mates with the mating surface of the self mating adhesive fasteners. They will not bond to surfaces which do not fit or mate with the mating surface of the self mating adhesive fasteners. An advantage of the invention is that a single self mating adhesive fastener element construction can be used in the formation of pairs of self mating fasteners.

Another advantage of the self mating adhesive fastener of the invention is that it can be constructed so that it is refastenable. Once the fastener has adhered to a mating surface, it can be pulled away without destroying its ability to adhere again to the same mating surface or another mating surface. To be considered refastenable, the self mating adhesive fastener should be capable of providing at least about 3 cycles of engagement and disengagement in a 24 hour period without suffering more than a 20% decrease in peel strength and without showing cohesive failure. Preferably, the self mating adhesive fastener should be capable of providing at least about 25 cycles, and more preferably at least about 50 cycles, of engagement and disengagement in a 24 hour period without suffering more than a 20% decrease in peel strength and without showing cohesive failure. Cohesive failure refers to a breakdown or separation of the adhesive layer. In contrast, adhesive failure refers to a separation or lack of adhesion between the adhesive layer and another surface.

Figure 1:
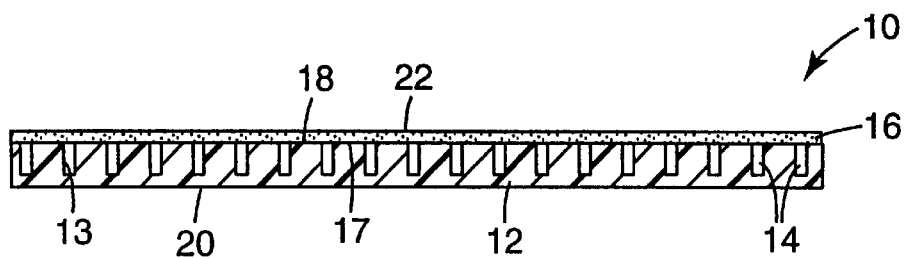
FIG. 1 is a schematic, cross sectional view of a self mating adhesive fastener element according to the present invention provided on a release liner.

Now referring to FIGS. 1–4, a self mating adhesive fastener element according to the present invention is provided at reference numeral 10. The self mating adhesive fastener element 10 includes posts 14 and adhesive layer 16. As shown in FIG. 1, an embossed liner 12 is provided. The embossed liner 12 includes an embossed release surface 18 and a second surface 20 which may or may not be a release surface. The adhesive layer 16 includes a substrate adhering surface 22 and a tacky surface 24. The substrate adhering surface 22 allows the self mating adhesive fastener 10 to become attached and affixed to a substrate 26.

Once the self mating adhesive fastener 10 is attached to a substrate 26, the embossed release liner 12 can be peeled away to expose the posts 14 and the tacky surface 24. As shown, the posts 14 extend away from the adhesive layer 16 thereby preventing contact of the tacky surface 24 with other surfaces. The exposed surface of the posts 14 and the tacky surface 24 can be referred to as the mating surface 15 because it is where the fastener element contacts other lastener elements and attaches thereto.

The posts 14 include three general regions. These regions include a base 50 where the posts 14 adhere to the adhesive layer 16, a tip or adhesive contacting surface 44 which is the portion of the posts that first engages or contacts the tacky surface of another fastener element, and an extension region 52 which separates the tacky surface 24 and the tip 44.

Figure 2:
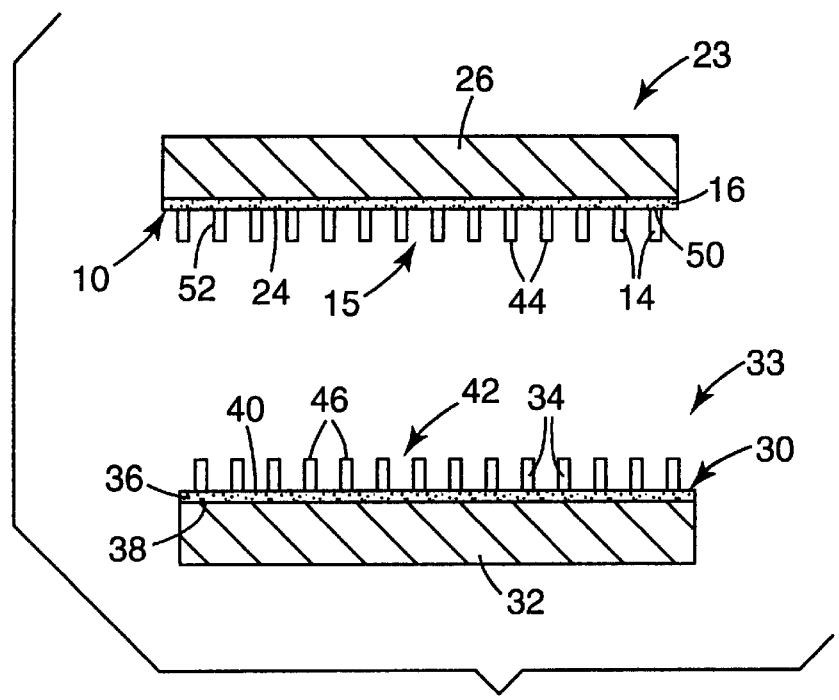
FIG. 2 is a schematic, cross sectional view of two articles provided with the self mating adhesive fastener of FIG. 1 in an open position.
Figure 3:
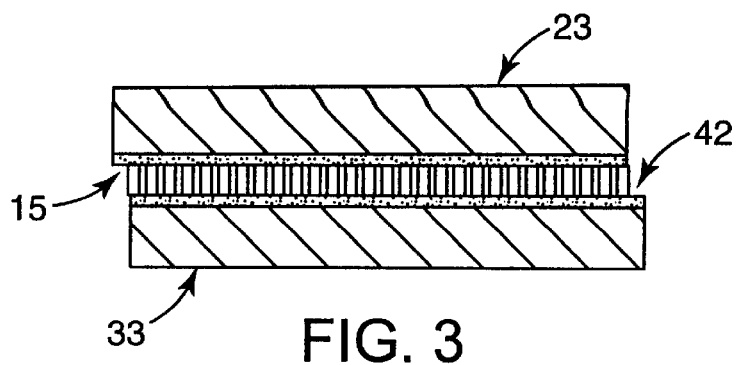
FIG. 3 is a schematic, cross sectional view of the two articles of FIG. 2 in a closed position.
Figure 4:
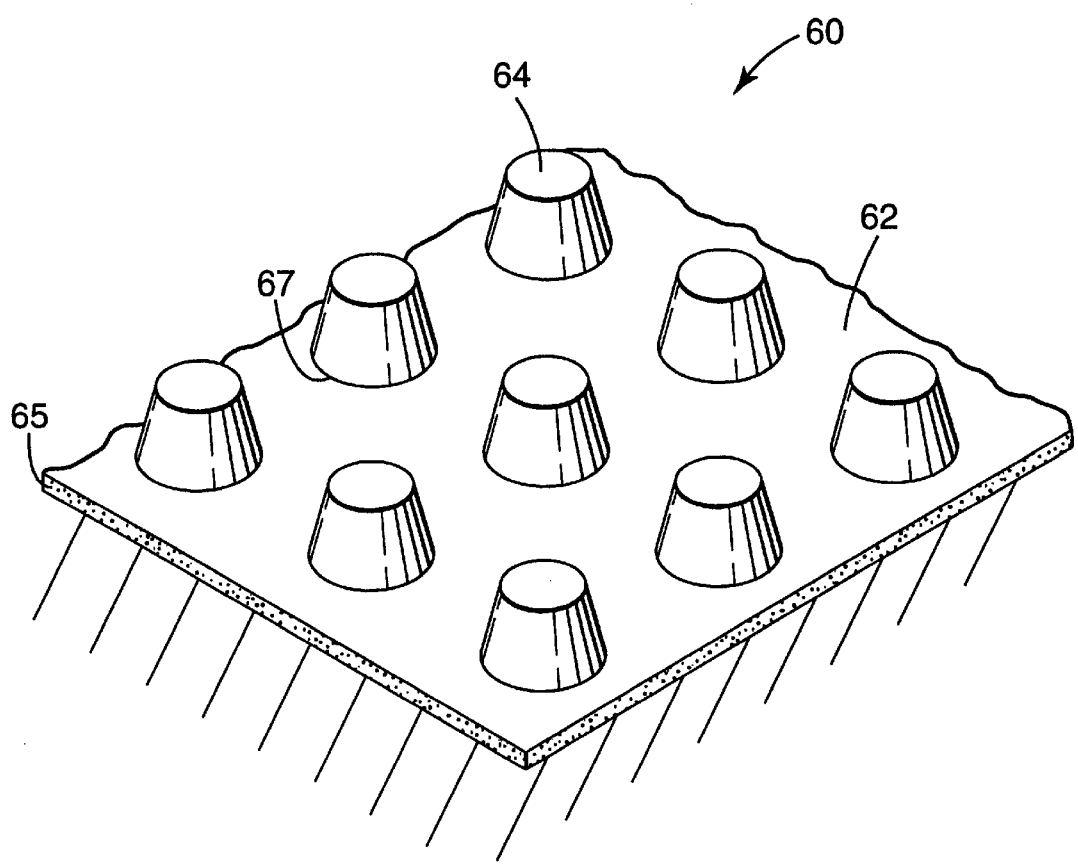
FIG. 4 is an isometric view of a self mating adhesive fastener element according to the present invention provided on a substrate.

As shown in FIGS. 2 and 3, the self mating adhesive fastener 10 can be applied to substrate 26. Similarly, a second substantially identical self mating adhesive fastener 30 is shown attached to another substrate 32. The self mating adhesive fastener 30 includes posts 34 and adhesive layer 36. The adhesive layer 36 includes a substrate adhering surface 38 and a tacky surface 40. The substrate adhering surface 38 allows the self mating adhesive fastener 30 to become attached and affixed to a substrate 32. The tip and extension region of posts 34 and the tacky surface 40 can be referred to as the mating surface 42.

The combination of the self mating adhesive fastener 10 and the substrate 26 can be referred to as the article 23. The combination of the self mating adhesive fastener 30 and the substrate 32 can be referred to as the article 33. Exemplary types of substrates include, but are not limited to, papers, plastics, metals, and ceramics. Exemplary articles include, but are not limited to, envelopes, clothing, textiles, closures, tapes, bag edges, and plastic parts for automobiles.

The mating surfaces 15 and 42 can be opposed as shown in FIG. 2, then engaged as shown in FIG. 3. When the mating surfaces 15 and 42 are not engaged, the fasteners can be referred to as being in the open position. When the mating surfaces 15 and 42 are engaged, the fasteners can be referred to as being in the closed position. When provided in the closed position, the tips 44 and 46 of posts 14 and 34 contact the tacky surfaces 40 and 24. In a preferred embodiment, tip 44 contacts the tacky surface 40, and tip 46 contacts the tacky surface 24.

The self mating adhesive fastener 10 can be manufactured by providing the embossed release liner 12 with recesses 13 and a land area 17. The recesses 13 are provided with a dimension or configuration which corresponds to the dimension or configuration of the posts 14. The land area 17 is the relatively flat portion of the embossed release liner 12 surrounding recesses 13. The pattern of the recesses 13 and the land area 17 can be adjusted to provide the fastener selectivity. An exemplary pattern of recesses and land area will provide a pattern of posts exemplified by the pattern 60 shown in FIG. 4 which shows tacky surface 62 and posts 64. The posts 64 have structures corresponding to the shape of the recesses in the liner, and the tacky surface 62 is relatively flat corresponding to the relatively flat land area of the embossed liner. In general, the posts 64 are arrayed in a spaced apart relationship to each other and are adhered to the adhesive 65 at their base 67 leaving the adhesive surface between the posts 64 as the tacky surface 62 for bonding to the post tips of an opposed adhesive fastener element.

A fluid material is applied over the release surface 18 of the embossed release liner 12, and allowed to fill the recesses 13. The fluid material is then cured, dried, or hardened to form the posts 14. Preferably, the material does not cover the land area 17 of the embossed release liner 12. This is so that the tacky surface 24 is exposed when the embossed release liner is peeled away. While some coverage of the material onto the land area 17 may be permitted, it is generally not desirable since it will cause a reduction in the surface area of the tacky surface 24. It is generally desirable for the tacky surface 24 to be sufficiently large to ensure sufficient adhesion when the fastener is provided in the closed position.

The degree of adhesion between opposed fastener units can be controlled by a number of factors. One factor includes adjusting the contact area between post tips of one fastener element and the tacky surface of an opposed fastener element. For example, it is expected that increasing the contact area between the post tips of a first fastener element and the tacky surface of an opposed fastener element will provide increased adhesion between fastener elements. Fastener elements which are intended to be less refastenable can be provided with more contact area between post tips and the tacky surface of an opposed fastener element. It should be understood that increasing the contact area between the post tips of a first fastener element and the tacky surface of an opposed fastener element is limited by the need for the fastener elements to nest. That is, as the number of posts provided by fastener elements increases, it is expected that it may become more difficult for the fastener elements to nest. In most applications, it is expected that, the posts of a fastener element will cover between about 20% and about 40% of the surface area of the adhesive layer, and more preferably between about 25% and about 35% of the surface area of the adhesive layer. It is expected that the posts of a fastener element will cover about one third of the surface area of the adhesive layer.

After the fluid material fills the recesses 13, an adhesive is applied over the posts 14 and the land area 17 to form the adhesive layer 16. It should be appreciated that the adhesive can be applied before or after the fluid material is cured to form the posts. The adhesive and the fluid material can be the same or different, and can be cured at the same time to increase bonding therebetween. In one embodiment of the invention, the adhesive material and the fluid material are the same material. In this situation, the adhesive layer 16 and the posts 14 are formed from an adhesive or adhesive forming material. The posts 14 can be treated so that they include nontacky areas (such as the tip) while the tacky surface 24 remains tacky. One exemplary way of treating the posts includes radiation curing. The embossed release liner can be provided so that the portion of the liner that forms the recesses is transparent to radiation while the land area is opaque to radiation. Radiation curing will cure at least the tips of the posts to provide a nontacky surface thereon.

The fastener 10 can be provided in a form suitable for storage and/or transportation. For example, it can be provided in the form of a roll or as a large sheet. In the case where the fastener 10 is provided in the form of a roll, it is generally desirable for the second surface 20 to be a release surface which contacts the substrate adhering surface 22, and can be peeled away from the substrate adhering surface 22 when it is desired to apply the fastener to a substrate. In this embodiment, the second release surface 20 should release from the substrate adhering surface 22 more readily than the embossed release liner 12 releases from posts 14 and the tacky surface 24. Alternatively, a separate release liner can be applied over the substrate adhering surface 22. When it is desired to use the self mating adhesive fastener 10, one can simply unroll the fastener to expose the substrate adhering surface 22. If a separate release liner is provided, that separate release liner can be peeled away to expose the substrate adhering surface. The self mating adhesive fastener 10 can then be applied to a substrate 26 and adhered thereto. When it is desired to expose the mating surface 15, the embossed liner 12 can be peeled away.

Post Materials

The posts, when cured, dried, hardened, etc., provide at least: a nontacky tip. Preferably, the exposed surface of the posts along the tip and extension region is nontacky. By nontacky, it is meant that the surface does not adhere on contact to other surfaces which do not exhibit tack. This feature allows the posts of opposed fasteners to slide by each other until the posts nest and the tips of the posts contact the tacky adhesive surface of the opposing fastener.

When it is desirable to provide fasteners which are refastenable, the tips of the posts should not permanently bond with the tacky surface of the opposed fastener. Once refastenable fasteners are engaged and provided in the closed position, it is desirable to separate the fasteners, without cohesive failure, so that they can later be re-engaged and provided in the closed position. While it is desirable to provide the fastener of the invention as a refastenable fastener, it should be understood that the fastener need not be refastenable. That is, the fastener of the invention can be provided so that when it is in the closed position, the bonding between the tip and the tacky surface can become permanent after a given amount of time, such as, 12 hours.

The posts 14 and the adhesive layer 16 of the self mating adhesive fastener 10 can be manufactured from the same or different material. In the situation where the posts and adhesive are different materials, it may be advantageous to apply a curable composition into the recesses 33 and then cure the composition to form the posts having a nontacky surface. Then the adhesive can be applied to provide the adhesive layer 16.

In the situation where the posts 14 and the adhesive 16 are the same material, the adhesion between the posts 14 and the adhesive layer 16 is strong enough to prevent cohesive failure. In the situation where the posts 14 are manufactured from a material different from that used to form the adhesive layer 16, enhancing the adhesion between the posts and the adhesive layer 16 may be important to ensure that the fastener element does not exhibit adhesive failure. It is necessary for the posts to remain in place on the adhesive layer while simultaneously being able to engage and disengage the tacky surface on the opposed fastener. The adhesion between the posts 14 and the adhesive layer 16 should be greater than the adhesion between the tips 44 of the posts 14 and the tacky surface on the opposed fastener. For permanent fasteners, the adhesion between posts and the adhesive layer and the tacky surface of the opposed fastener would be substantially comparable.

Whether the materials are used for forming the posts and the adhesive are the same or different, it may be advantageous to coat the post material, then the adhesive, and subject both to curing at the same time. It is expected that the adhesion between the posts and the adhesive will be stronger when they are concurrently cured as opposed to being sequentially cured.

Another way to ensure that posts remain adhered to the adhesive layer 16 while being able to disengage the tacky surface of the opposed fastener is to provide a contact area between the posts and the adhesive which is substantially greater than the contact area between the tops of the posts and the tacky surface of the opposed fastener. Accordingly, one preferred configuration of the posts would be to provide a truncated cone structure. Preferably, the surface area of the base to the surface area of the tip would be between a ratio of about 2:1 to about 4:1.

The posts are preferably provided with a configuration or structure which allows them to nest with the posts on an opposed fastener. In general, it is expected that the posts will be provided with the geometric shapes which may be characterized as truncated pyramids, cones, and triangular or square pyramids. It is generally preferred that the tips of the posts are truncated or relatively flat. The substantially flat surface of the tip allows good contact with the tacky surface of the opposed fastener. In addition, the substantially flat top of the post and/or the land area can be provided with a microstructure or other design which controls adhesion to certain types of adhesives. The introduction of microstructures described in International Publication No. WO 95/11945, published on May 4, 1995, which is incorporated herein by reference. The control of adhesion due to surface topography and contact area is discussed in the *Handbook of Pressure Sensitive Adhesive Technology*, 2nd Edition, edited by Donatas Satas, Van Nostrand Reinhold, 1989, which is incorporated herein by reference.

The configuration of a preferred post is controlled by a number of factors. Since the posts of the invention are preferably prepared by filling recesses in a release liner, the post height is somewhat limited by the thickness of the release liner. In addition, the height of the posts should not be so great as to introduce instability in bonding across the surface of the fastener. In general, it is expected that the posts will have a height of between about 75 and about 250 $\mu$m. For a post having a 125 $\mu$m height, that is the distance between the base and the tip, the base will preferably have a perimeter of between about 0.6 to about 3 mm, and the tip will preferably have a perimeter between about 0.4 to about 1.2 mm.

The self mating adhesive fasteners of this invention can have a wide range of properties depending on the selection of post materials and adhesive. The posts are preferably made from relatively nontacky material. In particular, it is preferred that the sides and the tip of the posts are nontacky. However, different post materials can provide a range in bonds to a specific adhesive. Likewise, for a given post material, different adhesives can provide a range in bonding for the fastener. In addition, such processing variables as adhesive thickness, adhesive to post contact area, and stiffness of the substrate are also variables that allow variation in disengagement forces.

It should be understood that a high density of posts can make it difficult for the posts of fastener elements to nest and contact the adhesive on the opposed fastener element. In other words, if there are too many posts, it is difficult for the posts to slip by each other so that the tops contact the tacky surface.

Materials suitable for forming the posts include those materials which can flow into the recesses provided in the embossed liner and then be cured, dried or hardened to provide a nontacky surface. Exemplary types of compositions which can be used to form the posts include thermoplastic polymer compositions, thermoset polymer compositions, actinic radiation curable compositions, and solvent containing compositions. While it is preferred that materials used to form the posts of the fastener elements of the present invention be applied in a flowable liquid form, some materials may also be applied as a flowable powder which subsequently melts and cures to form the posts. Preferred compositions includes epoxy resins, glass filled epoxy resins, and ultra violet light curable ink systems.

Embossed Liner

Embossed liners suitable for use in preparing fastener elements of the present invention encompasses a broad range of materials used as flexible carrier webs. A preferred material is a Kraft paper coated with a thermoplastic polymer such as polyethylene or polypropylene which can be thermally embossed to form recesses. Thermoplastic films that can be thermally embossed or cast onto a master surface that is formed with protrusions to be replicated to form recesses are also useful. Replicating techniques used to emboss the liners include those disclosed in coassigned U.S. Pat. No. 4,576,850 to Martens, the disclosure of which is incorporated herein by reference.

Adhesive

The type of adhesive which can be used in the self mating adhesive fastener of this invention should be selected to provide the desired properties for a given application. The adhesive can be non-tacky to the touch but aggressively tacky to other substrates. The adhesives can be substrate specific such as those described in International Publication No. WO 94/21742, published on Sept. 29, 1994, which is incorporated herein by reference.

Pressure sensitive adhesives are preferred for use in the embodiments of the present invention. Non-pressure sensitive adhesives such as thermally activated or solvent activated adhesives can be used, but they are less preferred than pressure sensitive adhesives. The benefits of a pressure sensitive adhesive include its natural flexibility and elongation properties. While the self mating fastener can employ a wide variety of known pressure sensitive adhesives, the pressure sensitive adhesive is preferably one that is aggressively tacky and forms strong bonds on contact with substrates.

A wide variety of coatable pressure sensitive adhesives can be used, such as, solvent coatable, melt-coatable, as well as latex-based pressure sensitive adhesives coated out of water. Also, solventless curable adhesives (often referred to as 100% solids) can be used. Where thicker adhesive coatings are desired, it may be desirable either to apply multiple layers of the adhesive or to photopolymerize an adhesive in situ. Specific examples of preferred types of adhesives include (meth)acrylates, e.g., isooctyl acrylate/acrylic acid co-polymers and tackified acrylate co-polymers; natural or synthetic rubber resins such as nitrile rubbers, e.g., acrylonitile/butadiene; silicone-based adhesives, e.g., polysiloxanes; polyolefins; polyesters; polyamides; and polyurethanes.

Conventional coating techniques utilized in the manufacture of adhesive tape constructions can be used to apply the adhesive composition. These techniques include, but are not limited to, knife coating, roll coating, hot melt coating, reverse roll coating, and gravure coating techniques. The resulting coating is then passed through an oven to remove the solvent or water to produce the adhesive construction. Alternatively, a solventless, curable adhesive can be applied to the carrier film using knife coating or metered coating techniques similar to those described above and subsequently cured to an adhesive state by exposure to actinic radiation, ultraviolet radiation or heat.

The self mating adhesive fastener of the present invention can be attached to those types of substrates where it is desired to provide selective attachment. Resulting articles include, but are not limited to, envelopes, clothing, textiles, closures, and plastic parts for automobiles. It should be understood that the self mating adhesive fastener is particularly advantageous as a substitute for hook-and-loop type fasteners. An advantage of the self mating adhesive fastener of the invention is that it does not require a second operation (adhesive coating, sewing, etc.) for convenient application of the fastener to substrates. The application is simply made by adhesion whereas hook-and-loop type fasteners must be adhesive coated or sewn to provide attachment to substrates that are to be fastened.

Objects and advantages of this invention are further illustrated by the following examples. The particular materials and amounts thereof recited in these examples as well as other conditions and details, should not be construed to unduly limit this invention. All materials are commercially available except where stated or otherwise made apparent.

EXAMPLE 1

The glossy side of a paper liner coated on both sides with polypropylene (0.13 mm thick glossy polypropylene, 0.13 mm thick matte polypropylene on standard 110 g/m² base paper available from Schoeller Technical Papers, Pulaski, N.Y.) was embossed to provide 225 recesses per square cm arranged in a hexagonal array. Each recess was an inverted truncated cone 350 µm in diameter at the surface and 200 µm in diameter at its depth of 100 m. These recesses were filled with an uncured mixture of EPI-REZ 35201 (waterborne epoxy resin available from Rhône-Poulenc, Louisville, K.Y.), 57% parts per hundred resin of EPI-CURE 872 (available from Rhône-Poulenc, Louisville, K.Y.), and 57% by weight glass bead fines (varying in size from 35 µm to 50 µm in diameter). This material was coated in the recesses of the liner, and the land area surface was wiped clean. The coated liner was placed in an oven at 60° C. for 10 minutes to remove solvent and then at 80° C. for 10 minutes to completely cure the epoxy.

The embossed side of the liner, containing the cured post material in the recesses, was then coated with an adhesive solution consisting of: 100 parts by weight of a resin solution of 2-methylbutylacrylate-acrylic acid (90:10) copolymer and ethyl acetate combined at a solids content of 37% plus 0.6 parts crosslinker consisting of a 5% solution of 1,1'-(1, 3-phenylenedicarbonyl)bis-(2-methylayiridine) in toluene. A coating gap of 51 µm was se-t in a knife bed coater and the liner was pulled through the gap to coat the adhesive-. The adhesive coated liner was placed in a 60° C. oven for 10 minutes to remove the solvent. This provided the PSA (pressure sensitive adhesive) for this example.

The adhesive was laminated to a 51 µm thick coextruded two-layer film; one layer consisting of a blend of polypropylene and poly(ethylene terephthalate) (PET), and the second layer being poly(ethylene terephthalate). For the blend layer, about 27 parts (27% by wt.) FINA 3230 polypropylene (available from Fina Oil and Chemical Co.) having a melt flow index (WI) of 1.6 was fed to the input of a 11.4 cm single-screw extruder. A volumetric solids feeder was used to control the rate of addition of FINA 3230 polypropylene fed to the blend layer. An additional feed stream of about 73 parts (73% by wt.) pre-dried, extrusion grade poly(ethylene terephthalate), with an intrinsic viscosity (I.V.) of about 0.59 g/dl and a melt point of about 235° C. (determined as the maximum in the melting peak of the second heating scan taken at 20° C./min. using a Perkin-Elmer DSC7), was fed to the input of the 11.4 cm single-screw extruder. The total feed rate of the 11.4 cm extruder was about 190 kg./hr. For the poly(ethylene terephthalate) layer, the same pre-dried extrusion grade poly(ethylene terephthalate) used in the blend layer was fed to the input of a 6.4 cm single-screw extruder. The feed rate of the 6.4 cm extruder was about 27.3 kg/hr. The 11.4 cm extruder and 6.4 cm extruder melt streams were combined using a three-layer feedblock configured to produce a two-layer construction. The feedblock was mounted to a 46 cm wide slot-fed sheeting die with a die gap of about 1 mm. A filter for particulate control and a gear pump for flow rate control were installed between the extruder gate and feedblock for both the 11.4 cm extruder and 6.4 cm extruder melt streams. The sheet formed by the die was cast onto a temperature controlled casting wheel maintained at a temperature of about 38° C. and the cast sheet was; held in place by electrostatic pinning. A finished film was then made using conventional polyester film biaxial orientation equipment to stretch the film in the machine direction (MD) about 3.0 times by preheating the cast web to about 82° C. and thien stretching at a temperature of about 88° C. and then to stretch the film in the transverse direction (TD) about 3.0 times at a temperature of about 107° C. The stretched film was then subjected to a heat set temperature of about 107° C. The stretched film was then subjected to a heat set temperature of about 232° C. while the film was restrained. Voids were created in the blend layer during film orientation resulting in an opaque, low density film. The finished film was 130 µm thick with a density of about 0.80 g/cc.

Figure 5:
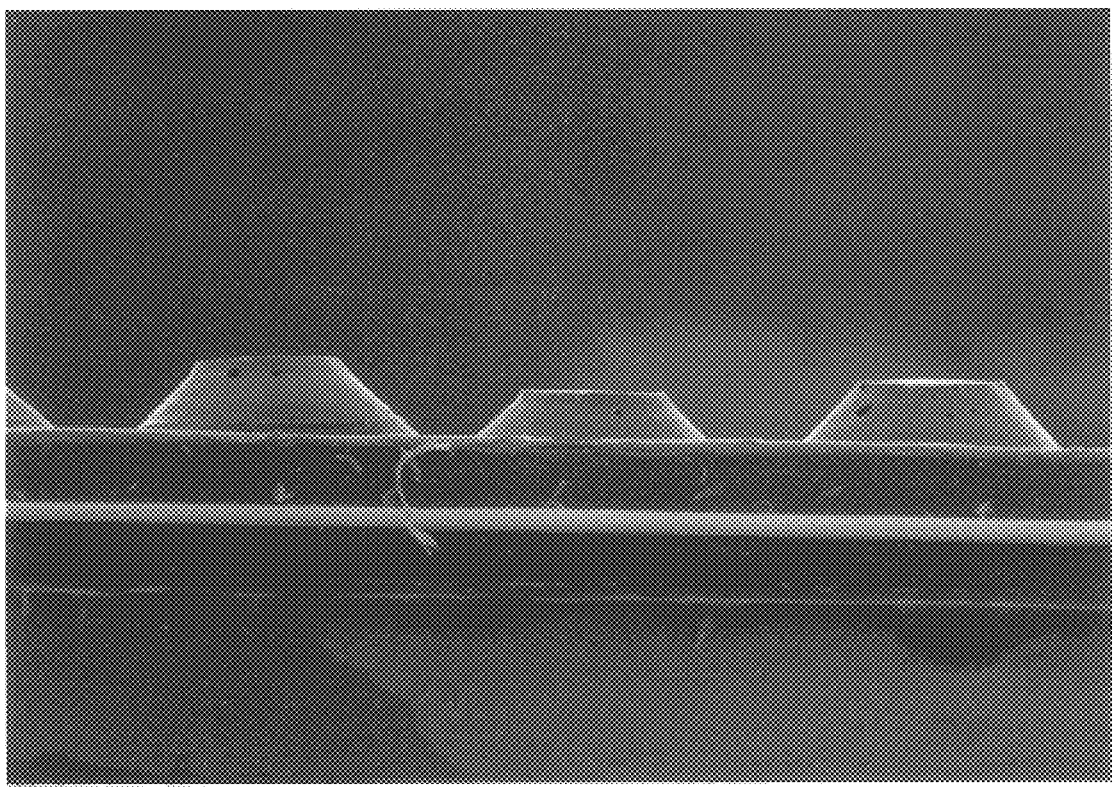
FIG. 5 is a scanning electron micrograph of the self mating adhesive fastener of Example 1.
Figure 6:
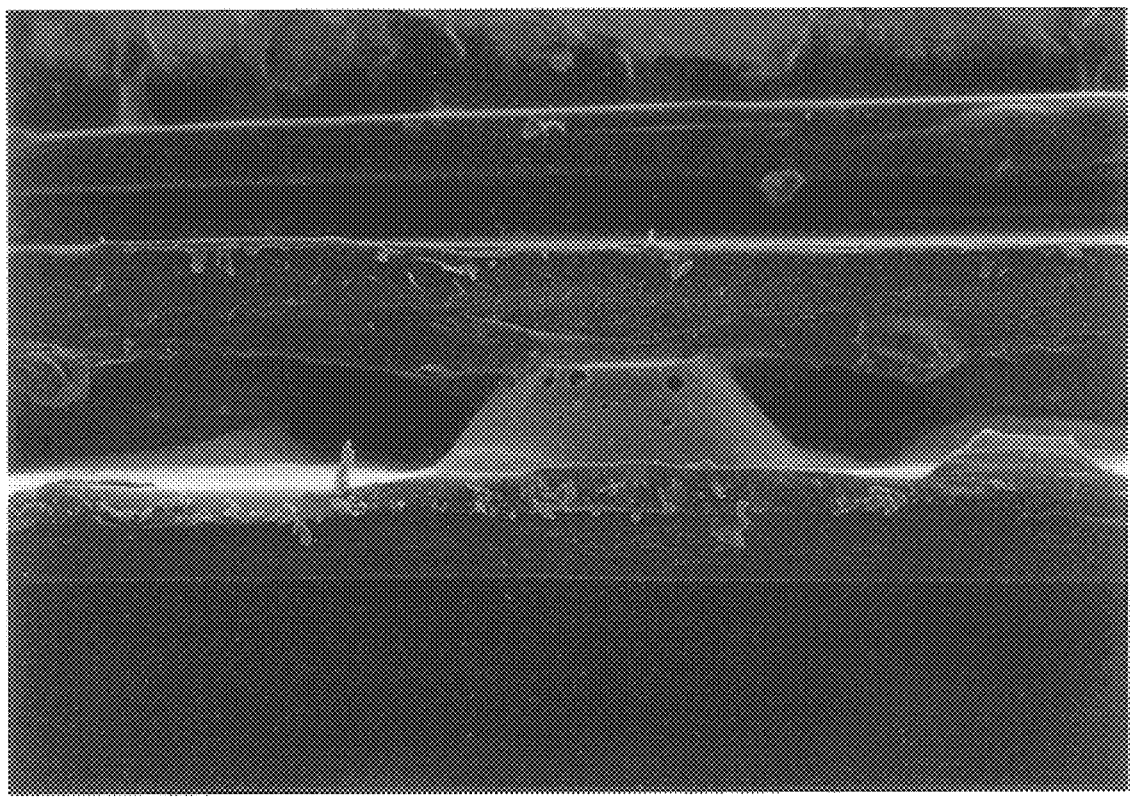
FIG. 6 is a scanning electron micrograph of the self mating adhesive fastener of Example 1 in a closed position.

The paperlike film provided the substrates for this example. When the embossed liner was removed, the adhesive on the film pulled the epoxy/bead mixture out of the recesses to form a self-mating fastener with nontacky, flat topped posts (FIG. 5). After engagement, the tops of the posts of each side of the fastener attached to the adhesive of the other side (FIG. 6). The posts also prevented adhesive to adhesive contact and, thus, permanent bonding from occurring.

EXAMPLE 2

A sample was prepared in the same manner as Example 1, except that a UV curable ink (No. 9720 overprint clear from SCOTCHCAL Series 9700 UV Curable Printing Inks, available from 3M, St. Paul, Minn.) was used to fill the recesses of the embossed liner. The ink was cured by passing the sample through a UV processor (model number QC1202A/NSPL manufacture by Radiation Polymer Co., Plainfield, Ill.) twice at a rate of 80 ft./min. at dosage rates of 0.076 J/cm² UVA, 0.07 J/cm² UVB, 0.006 j/cm² UVC, and 0.035 J/cm² UVV, as measured by UV Power Puck available from EIT, INC., Sterling, Va.

After curing the material in the recesses, the liner was coated with the adhesive of Example 1. A coating gap of 110 μm was set in a knife bed coater and the liner was pulled through the gap to coat the adhesive. The adhesive coated liner was placed in a 67° C. oven for 10 minutes to remove the solvent. This provided the PSA for this example.

The adhesive was laminated to a 51 μm thick film as described in Example 1. The film provided the substrates for this example. When the embossed liner was removed, the adhesive on the paperlike film pulled the UV cured ink out of the recesses to form a self-mating fastener with nontacky, flat topped posts. After engagement, the tops of the posts of each side of the fastener attached to the adhesive of the other side. The posts also prevented adhesive to adhesive contact and, thus, permanent bonding from occurring.

EXAMPLE 3

The recesses of the embossed liner of Example 1 were filled with an uncured mixture of 30 g of resin (EPO-KWICK No. 20-8136-128, available from Buehler, Lake Bluff, Ill.) and 6 g of hardener (EPO-KWICK No. 20-8136-032, also from Buehler) plus 90 g of about 50 μm glass beads using the procedures of Example 1. The embossed liner was then placed in an oven at 67° C. for 1 hour to cure the epoxy/glass bead mixture. After cooling to room temperature, the liner was coated with an adhesive solution consisting of equal parts of KRATON 1107 resin (available from Shell Chemical Company, Westbrook, Ill.) and WINGTAC 95 PLUS resin (available from Goodyear Tire and Rubber Company, Akron, Ohio) to provide 40 percent solids in toluene. This adhesive solution was coated using a knife bed coater with a gap of 125 μm. The adhesive solution was air dried for about 5 minutes before being placed in an oven at 90° C. for 30 minutes. After cooling to room temperature, the pressure sensitive adhesive was laminated to a sheet of 50 μm thick KAPTON film (a polyimide film available from E.I. duPont de Nemours and Company, Inc., Wilmington, Del.). The KAPTON film served as the substrate for this example. When the embossed liner was removed, the adhesive on the KAPTON film pulled the epoxy/glass bead mixture out of the recesses to form a self mating fastener with nontacky, flat topped posts (similar to that shown in FIG. 5). After engagement, the tops of the posts of each side of the fastener attached to the adhesive of the other side (similar to that shown in FIG. 6). The posts also prevented adhesive to adhesive contact and, thus, permanent bonding from occurring.

The fasteners of Examples 1–3 demonstrated good self mating properties. The posts of the fastener elements intermeshed well. It is expected that scanning electron micrographs of the fasteners of Examples 2 and 3 would look similar to the scanning electron micrographs of FIGS. 5 and 6.

Although the invention has been described with respect to specific preferred embodiments, it should be appreciated that other embodiments utilizing the concept of the present invention are possible without departing from the scope of the invention. The invention, for example, is not intended to be limited to these specific adhesive articles disclosed in the preferred embodiments. The invention is not intended to be limited to the preferred embodiments described herein, but rather the invention is defined by the claims and equivalents thereof

What is claimed is:

1. A self mating adhesive fastener element comprising:
   (a) a plurality of posts each having a base, an extension region, and a tip, the posts being arranged to provide a self mating pattern and fastener selectivity, and wherein the extension region and the tips are nontacky; and
   (b) an adhesive layer comprising a first surface and a second surface, wherein the bases of the posts are attached to the first adhesive layer surface and the first adhesive surface providing art adhesive surface between the posts, and said second surface provided for adhering to a substrate.

2. A self mating adhesive fastener element according to claim 1, further comprising a release liner contacting the posts and the tacky surface of the adhesive layer.

3. A self mating adhesive fastener element according to claim 1, wherein the tips of the posts include a substantially flat surface.

4. A self mating adhesive fastener element according to claim 3, wherein the substantially flat surface is microstructured.

5. A self mating adhesive fastener element according to claim 1, wherein the posts have a height of between about 75 to about 250 μm as measured from base to tip.

6. A self mating adhesive fastener element according to claim 1, wherein the posts have a perimeter of about 0.6 to about 3 mm at the base and a perimeter of about 0.4 to about 1.2 mm at the tip.

7. A self mating adhesive fastener element according to claim 1, wherein the posts have a truncated cone shape.

8. A self mating adhesive fastener element according to claim 1, wherein said posts are formed from a composition selected from the group consisting of a thermoset polymer composition, a thermoplastic polymer composition, an actinic radiation curable composition, and a solvent containing composition.

9. A self mating adhesive fastener element according to claim 8, wherein the posts further comprise a filler.

10. A self mating adhesive fastener element according to claim 8, wherein the thermoset polymer composition comprises an epoxy polymer.

11. A self mating adhesive fastener element according to claim 1, wherein the adhesive is a pressure sensitive adhesive.

12. A self mating adhesive fastener element according to claim 11, wherein the pressure sensitive adhesive is selected from the group consisting of acrylates, siloxanes, polyolefins, natural rubber based adhesives, block copolymer based adhesives, and mixtures thereof.

13. A self mating adhesive fastener element according to claim 1, further comprising an adhesive release liner contacting the second surface of said adhesive layer.

14. A self mating adhesive fastener element according to claim 13, wherein said self mating adhesive fastener element is provided in a roll construction.

15. An article comprising a substrate and a self mating adhesive fastener element adhered thereto, the self mating adhesive fastener element comprising:
   (a) a plurality of posts each having a base, an extension region, and a tip, the posts being arranged to provide a self mating pattern and fastener selectivity, and wherein the extension region and the tips are nontacky; and
   (b) an adhesive layer comprising a first surface and a second surface, wherein the bases of the posts are attached to the first adhesive layer surface and the first adhesive surface providing an adhesive surface between the posts, and said second surface provided for adhering to a substrate.

16. An article according to claim 15, further comprising a release liner contacting the posts and the tacky surface of the adhesive layer.

17. An article according to claim 16, wherein the tips of the posts include a substantially flat microstructured surface.

18. An article according to claim 15, wherein said substrate is selected from the group consisting of paper, plastic, metal and ceramic.

19. A method for using a self mating adhesive fastener element, the method comprising steps of:
  (a) providing a self mating adhesive fastener element comprising:
    (i) a plurality of posts each having a base, an extension, and a tip, the posts being arranged to provide a self mating pattern and fastener selectivity, and wherein the extension region and the tips are nontacky;
    (ii) an adhesive layer comprising a first surface and a second surface, said first surface provided for adhering to the bases of the posts and having a tacky surface between the posts, and said second surface provided for adhering to a substrate; and
  (b) applying said second surface of the adhesive layer to a substrate.

20. A method for using a self mating adhesive fastener element according to claim 19, wherein said self mating adhesive fastener further includes a release liner covering the posts and the tacky surface of the adhesive layer, and said method includes a step of:
  (a) peeling the release liner away from the posts and the tacky surface of the adhesive layer to expose a mating surface.

\* \* \* \* \*

UNITED STATES PATENT AND TRADEMARK OFFICE
CERTIFICATE OF CORRECTION

PATENT NO.    : 6,159,596
DATED         : December 12, 2000
INVENTOR(S)   : Calhoun, Clyde D.

It is certified that error appears in the above-identified patent and that said Letters Patent is hereby corrected as shown below:

Column 1,
Line 60, delete "filting" and insert in place thereof -- fitting --.

Column 2,
Line 56, delete "mating", and insert in place thereof -- mating --.

Column 3,
Line 37, insert -- . -- after "itself".
Line 46, delete "," after "be".

Column 4,
Line 26, delete "lastener" and insert in place thereof -- fastener --.

Column 5,
Line 45, delete "," after "that".

Column 6,
Line 27, delete ":" after "least".

Column 9,
Line 48, delete "57%" and insert in place thereof -- 5.75 --.
Line 63, delete "se-t" and insert in place thereof -- set --.
Line 64, delete "adhesive-" and insert in place thereof -- adhesive --.

Column 10,
Line 32, delete ";" after "was".
Line 36, delete "thien" and insert in place thereof -- then --.

UNITED STATES PATENT AND TRADEMARK OFFICE
CERTIFICATE OF CORRECTION

PATENT NO.    : 6,159,596
DATED         : December 12, 2000
INVENTOR(S)   : Calhoun, Clyde D.

It is certified that error appears in the above-identified patent and that said Letters Patent is hereby corrected as shown below:

<u>Column 12,</u>
Line 6, delete "art" and insert in place thereof -- an --.

Signed and Sealed this

Twenty-first Day of January, 2003

JAMES E. ROGAN
*Director of the United States Patent and Trademark Office*